United States Patent
Zhang et al.

(10) Patent No.: US 7,615,655 B2
(45) Date of Patent: Nov. 10, 2009

(54) PROCESS FOR THE PRODUCTION OF ALKYLENE OXIDE USING A GAS-PHASE PROMOTER SYSTEM

(75) Inventors: Liping Zhang, Hurricane, WV (US); Hwaili Soo, Charleston, WV (US); Juliana G. Serafin, Charleston, WV (US)

(73) Assignee: Dow Global Technologies, Inc., Midland, MI (US)

( * ) Notice: Subject to any disclaimer, the term of this patent is extended or adjusted under 35 U.S.C. 154(b) by 597 days.

(21) Appl. No.: 10/571,508

(22) PCT Filed: Aug. 9, 2004

(86) PCT No.: PCT/US2004/025906
§ 371 (c)(1),
(2), (4) Date: Mar. 10, 2006

(87) PCT Pub. No.: WO2005/035513
PCT Pub. Date: Apr. 21, 2005

(65) Prior Publication Data
US 2007/0032670 A1  Feb. 8, 2007

Related U.S. Application Data

(60) Provisional application No. 60/507,011, filed on Sep. 29, 2003.

(51) Int. Cl.
*C07D 301/10* (2006.01)
(52) U.S. Cl. ............................................. 549/534
(58) Field of Classification Search ............ 549/534
See application file for complete search history.

(56) References Cited

U.S. PATENT DOCUMENTS

| | | | |
|---|---|---|---|
| 2,040,782 A | 5/1936 | van Peski | |
| RE20,370 E | 5/1937 | Lefort | |
| 4,831,162 A | 5/1989 | Nakajima et al. | |
| 4,837,194 A | 6/1989 | Hayden | |
| 4,994,587 A | 2/1991 | Notermann et al. | |
| 4,994,588 A | 2/1991 | Kapicak et al. | |
| 4,994,589 A | 2/1991 | Notermann | |
| 5,187,140 A | 2/1993 | Thorsteinson et al. | |
| 5,387,751 A * | 2/1995 | Hayden et al. | ............ 549/534 |
| 5,504,053 A | 4/1996 | Chou et al. | |
| 6,511,938 B1 | 1/2003 | Liu et al. | |

FOREIGN PATENT DOCUMENTS

| | | |
|---|---|---|
| EP | 0003642 | 7/1984 |
| EP | 0176253 | 3/1990 |
| EP | 480537 * | 4/1992 |
| EP | 0425020 B1 | 2/1999 |
| GB | 2161480 A | 6/1985 |
| WO | WO-03/044002 A1 | 5/2003 |
| WO | WO-03/044003 A1 | 5/2003 |

OTHER PUBLICATIONS

Berty, J. M., Applied Industrial Catalysis, 1983, pp. 224-227, vol. 1, Chapter 8.
Kirk-Othmer, Encyclopedia of Chemical Technology, 1994, pp. 915-959, 4th Edition, vol. 9.

* cited by examiner

*Primary Examiner*—Bernard Dentz

(57) ABSTRACT

An improved process for the manufacture of ethylene oxide through the epoxidation of ethylene using a catalyst comprising silver and at least one efficiency-enhancing salt of a member of a redox-half reaction pair. Added to the epoxidation reaction is a two-component gas-phase promoter system comprising a chlorine-containing component (for example ethyl chloride, methyl chloride, vinyl chloride and ethylene dichloride), and a nitrogen-containing component of nitric oxide and other compounds capable of generating under reaction conditions at least one gaseous efficiency-enhancing member of a redox-half reaction pair comprising NO, $NO_2$, $N_2O_3$ or $N_2O_4$. The amount of each component of said gaseous promoter is adjusted to maintain the ration of N* to Z* less than or equal to 1 wherein, N* is the nitric oxide equivalent in ppmv, ranging from 1 to 20 ppmv and Z*=ethyl chloride equivalent (ppmv)*100 percent/ethane equivalent (mol percent)*100 ranging from 5 to 40 ppmv.

7 Claims, No Drawings

PROCESS FOR THE PRODUCTION OF ALKYLENE OXIDE USING A GAS-PHASE PROMOTER SYSTEM

CROSS-REFERENCE TO RELATED APPLICATION

This application is a 371 of PCT/US2004/025906 filed 09 Aug. 2004, which claims the benefit of U.S. Provisional Application Ser. No. 60/507,011, filed Sep. 29, 2003.

FIELD OF INVENTION

This invention relates to gaseous promoter systems designed to enhance the performance of catalysts used in the epoxidation of ethylene to ethylene oxide. More particularly, this invention relates to a gaseous promoter system which uses the synergy between two gaseous modifiers: the gaseous nitrogen-containing components capable of generating at least one efficiency-enhancing member of a redox-half reaction pair and the gaseous chlorine-containing components.

BACKGROUND OF THE INVENTION

The production of alkylene oxide, such as ethylene oxide, by the reaction of oxygen or oxygen-containing gases with ethylene in the presence of a silver-containing catalyst at elevated temperature is an old and well-known art. For example, U.S. Pat. No. 2,040,782, dated May 12, 1936, describes the manufacture of ethylene oxide by the reaction of oxygen with ethylene in the presence of silver catalysts which contain a class of metal-containing solid promoters. In Reissue U.S. Pat. 20,370, dated May 18, 1937, Leforte discloses that the formation of olefin oxides may be effected by causing olefins to combine directly with molecular oxygen in the presence of a silver catalyst. (An excellent discussion on ethylene oxide, including a detailed description of commonly used manufacturing process steps, is found in Kirk-Othmer's *Encyclopedia of Chemical Technology*, 4$^{th}$ Ed.(1994) Volume 9, pages 915 to 959).

The catalyst is the most important element in direct oxidation of ethylene to produce ethylene oxide. There are several well-known essential components of such catalyst: silver; a suitable support/carrier (for example alpha-alumina); and promoters, all of which can play a role in improving catalyst performance. Because of the importance of the catalyst in the production of ethylene oxide, much effort has been expended to improve the performance of such catalysts.

The use of suitable promoters is an effective and proven way to enhance the performance of the catalyst in the production of alkylene oxide, for example ethylene oxide, and such use is well known to those skilled in the art. There are at least two types of promoters—solid promoters and gaseous promoters. A solid promoter is incorporated into the catalyst prior to its use, either as a part of the carrier (that is support) or as a part of the silver component applied thereto. When a solid promoter is added during the preparation of the catalyst, the promoter may be added to the carrier before the silver component is deposited thereon, added simultaneously with the silver component, or added sequentially following the deposition of the silver component on the carrier. Examples of well-known solid promoters for catalysts used to produce ethylene oxide include compounds of potassium, rubidium, cesium, rhenium, sulfur, manganese, molybdenum, and tungsten. During the use of the catalyst in the reaction to make ethylene oxide, the specific form of the promoter in the catalyst may be unknown.

In contrast, the gaseous promoters are gas-phase compounds and or mixtures thereof which are introduced to a reactor for the production of alkylene oxide (for example ethylene oxide) with vapor-phase reactants, such as ethylene and oxygen. Such promoters further enhance the performance of a given catalyst, working in conjunction with or in addition to the solid promoters.

It is well known that for catalysts using certain solid promoters, in particular those employing at least one efficiency-enhancing salt of a member of a redox-half reaction pair, the addition of a gaseous component capable of producing a member of a redox-half reaction pair is advantageous for maintaining selectivity and activity (see U.S. Pat. Nos. 5,387,751, 4,837,194, 4,831,162, 4,994,587, 4,994,589, 4,994,588, 5,504,053, 5,187,140, and 6,511,938 B1).

As used herein, the term "salt" does not require that the cation and anion components of the salt be associated with or bonded to one another in the solid catalyst, but rather implies that both components are present in some form in the catalyst under reaction conditions.

In the catalysts used in the process of the present invention, the gaseous component capable of producing a member of a redox-half reaction pair under reaction conditions is a nitrogen-containing gas, such as for example nitric oxide, nitrogen dioxide and/or dinitrogen tetroxide, hydrazine, hydroxylamine or ammonia, nitroparaffins (for example, nitromethane), nitroaromatic compounds (for example, nitrobenzene), N-nitro compounds, and/or nitriles (for example, acetonitrile). The amount of gaseous nitrogen-containing promoter to be used in these catalysts is that amount sufficient to enhance the performance, such as the activity of the catalyst and particularly the efficiency of the catalyst. The amount of gaseous nitrogen-containing promoter is generally described in the aforementioned patents as being determined by the particular efficiency-enhancing salt of a member of a redox-half reaction pair used and the concentration thereof, the particular alkene undergoing oxidation, and by other factors including the amount of carbon dioxide in the inlet reaction gases. For example, U.S. Pat. No. 5,504,053 discloses that when the gaseous nitrogen-containing promoter is NO (nitric oxide), a suitable concentration is from 0.1 to 100 ppm, by volume, of the gas stream. Preferably, when $CO_2$ (carbon dioxide) is present in amounts up to 3 volume percent, the NO is present in 0.1 to 60 ppmv, preferably 1 to 40 ppmv. Similarly, U.S. Pat. No. 5,387,751 discloses a continuous process for making ethylene oxide which comprises contacting ethylene, oxygen, a silver-containing catalyst and from 1 to 50 parts per million by weight of vinyl chloride reaction modifier with a nitrogen oxide in a concentration of 0.5 to 50 ppm of $NO_2$ equivalent of the process gas by volume, said nitrogen oxide forming nitrate and or nitrite ions in the catalyst under process conditions.

It is known in the catalyst literature that the concentration of gaseous chlorine-containing promoter (also referred to as modifier or inhibitor) which is required for optimum catalyst performance is dependent on the amounts of hydrocarbons present in the gas phase and other factors (J. M. Berty, *Applied Industrial Catalysis*, Vol. 1, Chapter 8, p. 224-227, 1983). The specific reactions by which hydrocarbons remove chloride from the catalyst surface are cited, and while ethane is reported to strip chlorides very effectively, ethylene is also capable of removing chlorides but is found to be significantly less effective. WO 03/044002 A1 and WO 03/044003 A1 disclose methods for optimizing gaseous promoters for high selectivity catalysts in reaction phases with differing feed compositions and temperatures, respectively. The optimum modifier level is proposed to depend on the effective molar quantity of the hydrocarbon present in the feed and the effective molar quantity of the active species of the reaction modifier.

Several terms are commonly used to describe some of the parameters of catalytic systems for epoxidation of alkenes. For instance, "conversion" is defined as the molar percentage of alkene fed to the reactor which undergoes reaction. Of the total amount of alkene which is converted to a different chemical entity in a reaction process, the molar percentage which is converted to the corresponding alkylene epoxide is known as the "efficiency" (which is synonymous with the "selectivity") of that process. The product of the percent efficiency times the percent conversion (divided by 100 percent to convert from percent$^2$ to percent) is the percentage "yield", that is, the molar percentage of the alkene fed that is converted into the corresponding epoxide.

The "activity" of a catalyst can be quantified in a number of ways, one being the mole percent of alkylene epoxide contained in the outlet stream of the reactor relative to that in the inlet stream (the mole percent of alkylene epoxide in the inlet stream is typically, but not necessarily, zero percent) while the reactor temperature is maintained substantially constant, and another being the temperature required to maintain a given rate of alkylene epoxide production. That is, in many instances, activity is measured over a period of time in terms of the molar percent of alkylene epoxide produced at a specified constant temperature. Alternatively, activity may be measured as a function of the temperature required to sustain production of a specified constant mole percent of alkylene epoxide. The useful life of a catalysts system is the length of time that reactants can be passed through the reaction system during which results are obtained which are considered by the operator to be acceptable in light of all relevant factors.

"Deactivation", as used herein, refers to a permanent loss of activity and/or efficiency, that is, a decrease in activity and/or efficiency which cannot be recovered. As noted above, production of alkylene epoxide product can be increased by raising the temperature, but the need to operate at a higher temperature to maintain a particular rate of production is representative of activity deactivation. The "stability" of a catalyst is inversely proportional to the rate of deactivation, that is, the rate of decrease of efficiency and/or activity. Lower rates of decline of efficiency and/or activity are generally desirable.

To be considered satisfactory, a catalyst must have acceptable activity and efficiency, and the catalyst must also have sufficient stability, so that it will have a sufficiently long useful life. When the efficiency and/or activity of a catalyst has declined to an unacceptably low level, typically the reactor must be shut down and partially dismantled to remove the catalyst. This results in losses in time, productivity and materials, for example, silver catalytic material and alumina carrier. In addition, the catalyst must be replaced and the silver salvaged or, where possible, regenerated. Even when a catalyst is capable of regeneration in situ, generally production must be halted for some period of time. At best, replacement or regeneration of catalyst requires additional losses in production time to treat the catalyst and, at worst, requires replacement of the catalyst with the associated costs. It is therefore highly desirable to find ways to lengthen the useful life of a catalyst.

SUMMARY OF THE INVENTION

One aspect of the present invention relates to a process for the manufacture of ethylene oxide through the epoxidation of ethylene in a reactor having at least one inlet for the introduction of raw materials and additives and at least one outlet for the discharge of ethylene oxide, which process comprises:

A) reacting a feed comprising ethylene, oxygen, and optionally ethane in the presence of a catalyst, said catalyst comprising a catalytically-effective amount of silver on an inert, refractory solid support and at least one efficiency-enhancing salt of a member of a redox-half reaction pair;

B) adding to said feed a two-component gas-phase promoter comprising at least one chlorine-containing component selected from a group consisting of ethyl chloride, methyl chloride, vinyl chloride and ethylene dichloride; and at least one nitrogen-containing component selected from a group consisting of nitric oxide and other compounds capable of forming under reaction conditions at least one gaseous efficiency-enhancing member of a redox-half reaction pair comprising NO, $NO_2$, $N_2O_3$ or $N_2O_4$;

C) adjusting the amount of each component of said gas-phase promoter to maintain the ratio of N* to Z* equal to or less than 1 wherein, N* is defined as the nitric oxide equivalent, in units of ppmv, having an numerical value from 1 to 20 ppmv and Z*=ethyl chloride equivalent (ppmv)×100 percent/ ethane equivalent (mol percent)×100 having an numerical value of 5 to 40 ppmv; and

D) controlling the temperature of said reactor from 200° C. to 300° C., and the pressure at the inlet of said reactor from 1000 to 2500 kPa (absolute), and the concentration of carbon dioxide at said inlet from 0 to 2 mole percent.

Another aspect of the present invention relates to a catalyst comprising from 5 to 50 percent by weight of silver based on the weight of the catalyst.

Yet another aspect of the present invention relates to the refractory solid support comprising alpha-alumina having morphology comprising interlocking platelets.

While the present invention should be understood as being unconstrained by any particular theory, it is believed that the gaseous nitrogen-containing promoter, when introduced to a reactor with gaseous chlorine-containing promoter, the solid catalyst, and other raw materials, such as ethylene and oxygen, improves the overall performance of the catalyst by affecting the amount of nitrogen-containing species on the catalyst surface which directly affects the efficiency of the catalyst. Chlorine-containing species also enhance efficiency. Both species have an optimum concentration determined by the balance between the promoting effect on efficiency and/or activity and/or stability, the blockage of sites for reaction, and the enhancement or inhibition of secondary reactions between the various species present in the system. The novel aspect of this invention is the recognition that the existence of these secondary reactions results in a correlation between the optimum of the gaseous nitrogen-containing promoter and the chlorine-containing promoter for catalysts comprising an efficiency-enhancing salt of a member of a redox-half reaction pair, which has not been previously recognized.

A key distinguishing feature of the present invention is the deployment of particularly advantageous amounts of the gaseous nitrogen-containing promoter and the gaseous chlorine-containing promoter to obtain a synergistic effect in enhancing the performance of the catalyst for the manufacture of ethylene oxide by the vapor-phase epoxidation of ethylene.

DETAILED DESCRIPTION OF THE INVENTION

It is preferred that the production of ethylene oxide using solid catalyst comprising silver is carried out in a gas-phase process in a reactor, in which the gaseous raw materials, or so-called inlet feed, are passed through a bed of the solid phase catalyst, which comprises silver and added promoter species. In this process, which is generally run continuously, gaseous promoters, sometimes called modifiers, inhibitors or enhancers, are added to the inlet gases used as raw materials for the production of ethylene oxide and other gases present in the system. The raw materials comprise ethylene and oxygen. Ethane and other hydrocarbons, sometimes including methane, may be added to control the gaseous chloride-containing promoter, as well as to change the thermal and chemical properties of the gas mixture and make the reaction easier to control. Carbon dioxide and water, produced as by-products of the reaction, are generally present from recycle of the reaction gases, or as impurities. Nitrogen and other inert gases, such as argon, may also be present. Nitrogen, methane or other gases making up the balance of the inlet feed are sometimes referred to as the ballast gas.

The reaction pressure varies depending on the design of the reactor, but is typically in the range of 1000 kPa to 2500 kPa absolute. Preferably, the pressure of the reactor is from 1800 to 2500 kPa absolute.

The temperature of the reactor is an important parameter with a useful range of 200° C. to 300° C. In the present invention, the preferred range of temperature for the reactor is from 210° C. to 280° C.

The ethylene concentration in the feed may vary over a wide range. Generally, the ethylene concentration will be from 18 to 35 mole percent, and preferably from 20 to 32 mole percent of the total feed. This concentration may be adjusted over the life of the catalyst for various reasons including catalyst performance and ease of operation.

The oxygen concentration in the feed is not material to this invention and may vary over a wide range. In practice, flammability of the reaction gases is a major consideration which may limit the oxygen concentration. Generally, the oxygen concentration will vary from 1 to 15 mole percent, and more typically from 2 to 12 mole percent of the total feed.

The carbon dioxide concentration in the feed has a large adverse effect on the efficiency, activity and/or stability of catalysts used in the present invention. Carbon dioxide is produced as a reaction by-product and may also be introduced with other inlet reaction gases as an impurity. In the present invention, the inlet carbon dioxide concentration is limited from 0 to 2 mole percent in the inlet feed gases. Water is also a by-product, and may be present in the feed gases in concentrations from 0 to 3 mole percent.

Besides ethylene, ethane or other hydrocarbons may act to dechlorinate the catalyst surface, and may thus be added to the feed gases to more easily control the amount of chloride-containing promoter. Some of these hydrocarbons may also be introduced as impurities in the ethylene feed or may be present for other reasons. Typically, the preferred concentration of ethane in the feed, when present, is from 0 to 2 mole percent.

Methane or nitrogen or another gas may be used to make up the bulk of the gas feed which is not raw materials, additives, by-products or impurities. In such situations, the inert gas used, that is the ballast gas, ranges from 50 to 80 mole percent of the feed gases, except during start-up or shutdown when concentrations may vary widely. Other hydrocarbons may also be used as the ballast gas.

In the process of making ethylene oxide in the present invention, the inlet gases specified herein are mixed together with the two gaseous promoters, that is the nitrogen-containing promoter and the chlorine-containing promoter. The order in which the inlet gases and promoters are mixed together is not critical to the present invention, and they may be mixed simultaneously or sequentially. The order of mixing of the gaseous components of the process may be chosen for convenience or for safety reasons. For example, oxygen is generally added after the ballast gas for reasons of safety. It is only critical that both gaseous promoters are present in the inlet feed introduced to the reactor containing the solid catalyst. After introduction of the inlet feed gases to the solid catalyst in the reactor operating at the specified pressure and temperature, it has been discovered in this invention that it is desirable to adjust the effective concentrations of the two gaseous promoters to a particular range of ratios in order to obtain the highest performance of catalyst in the production of ethylene oxide.

It is known in the art that catalysts having a particularly high efficiency require the use of a gaseous nitrogen-containing promoter that subsequently provides a member of a redox-half reaction pair, in addition to a gaseous chlorine-containing promoter, and at least one efficiency-enhancing salt of a member of a redox-half reaction pair in the solid catalyst.

The gaseous nitrogen-containing promoter added to the inlet feed to provide a member of a redox half-reaction pair may be chosen from nitric oxide, nitrogen dioxide, dinitrogen tetroxide, hydrazine, hydroxylamine, ammonia, nitroparaffins (for example, nitromethane), nitroaromatic compounds (for example, nitrobenzene), N-nitro compounds, nitriles (for example, acetonitrile) and/or mixtures thereof. The efficacy of each of these compounds as a promoter in the desired reaction to ethylene oxide is dependent on its ability to provide a nitrogen and oxygen-containing species to the catalyst, and in particular on the ability of the compound to generate $NO$, $NO_2$, $N_2O_3$ and or $N_2O_4$ in the reactor. Under reaction conditions, interconversion of the nitrogen and oxygen-containing species may occur and more than one of the species $NO$, $NO_2$, $N_2O_3$ and $N_2O_4$ may be present.

While the present invention should be understood as being unconstrained by any particular theory, it is believed that optimum catalyst performance depends on both the concentration of the gaseous nitrogen-containing promoter and the concentration of the gaseous chlorine-containing promoter due to the existence of particular chemical reactions between nitrogen-containing species, chlorine and/or chlorine-containing species and/or solid promoter components of the catalyst under reaction conditions. While most of these reactions take place on the catalyst surface, some may also take place within the catalyst or in the gas phase.

The effective amount (the amount that actually participates in the reactions in the catalyst during the process of making ethylene oxide) of the gaseous promoters is not necessarily the same as the actual amount of promoter introduced into the inlet feed. The effective amount of nitrogen-containing promoter depends on the pressure, amount of carbon dioxide, operating temperature and catalyst properties such as catalyst age. The effective amount of chlorine-containing promoter depends on the amount of hydrocarbons which are capable of removing chlorine from the catalyst surface, and the operating temperature. In addition, the different compounds which may be used as a gaseous promoter have differing levels of effectiveness. The effectiveness of a particular gaseous nitrogen-containing promoter is determined by its ability to generate the active nitrogen and oxygen-containing members of a redox half reaction pair in the catalyst. The effectiveness of a particular chlorine-containing gaseous promoter is dependent on its ability to deposit particular chlorine species, for example atomic chlorine or chloride ions, in the catalyst.

As used herein, the term "in the catalyst" includes the surface of the catalyst, the interior of the catalyst (that is subsurface), and or the gas phase above the catalyst.

In view of the foregoing discussion, it is essential to determine experimentally the effectiveness of the gaseous promoter to be used in the process of this invention. For the nitrogen-containing promoters, nitric oxide (NO) is used as the standard compound against which the relative effectiveness of other nitrogen-containing compounds is measured. The reactor pressure also has an impact on the effectiveness of the nitrogen-containing promoters and must therefore be taken into consideration. In the present invention, $N^*$ is a measure of the overall effectiveness of the nitrogen-containing promoters and is defined as:

$$N^* = \text{nitric oxide equivalent}(ppmv)$$

If NO is the only gaseous nitrogen-containing promoter present in the inlet, $N^*$ is the inlet NO concentration in ppmv multiplied by the inlet pressure in kiloPascals, absolute, divided by 2300 kPa. When another nitrogen-containing promoter is used alone or in conjunction with NO, the nitric oxide equivalent is the concentration of NO in ppmv plus the concentration of the other gaseous nitrogen-containing promoter (corrected for its effectiveness as a promoter as compared to NO) times the inlet pressure in kiloPascals, absolute, divided by 2300 kPa. The relative effectiveness of a non-NO promoter can be measured experimentally by replacing NO with the other promoter and determining the concentration needed to obtain the same level of catalyst performance provided by NO. As a way of further illustration, if the required concentration of $NH_3$ at the reactor inlet is 1.5 ppmv to realize equivalent effectiveness in terms of catalyst performance provided by 1 ppmv NO, then the nitric oxide equivalent for 1 ppmv $NH_3$ would be 0.67 ppmv NO. For a hypothetical feed of 1 ppm NH3 and 1 ppm NO, $N^*$ would then be (1+0.67 ppmv) times the inlet pressure in kiloPascals, absolute, divided by 2300 kPa. In determining the relative effectiveness of gaseous nitrogen-containing promoters, it is necessary to use the same inlet conditions as those which will be used in the process to make ethylene oxide because the relative effectiveness may be somewhat dependent on the concentrations of the other gases in the feed and temperature.

In the present invention, the useful range of concentration of the nitrogen-containing gas phase promoter, expressed as $N^*$, is from 1 to 20 ppmv.

It is well known in the art that gaseous chlorine-containing promoters, such as ethyl chloride, vinyl chloride, ethylene dichloride, methyl chloride, and other chlorine-containing hydrocarbons; may be added to enhance the efficiency of the solid catalyst. It is also known that hydrocarbons, such as ethane, propane, and ethylene, dechloride the surface of the solid catalyst and thereby act to decrease the effectiveness of the chloride-containing promoters. Thus, in order to usefully control the amount of chlorine present on the solid catalyst, $Z^*$, the measure of the overall effectiveness of the chlorine-containing promoter, is defined as:

$$Z^* = \frac{\text{ethyl chloride equivalent}(ppmv) \times 100 \text{ percent}}{\text{ethane equivalent}(\text{mol precent}) \times 100}$$

If ethyl chloride is the only gaseous chloride-containing promoter present in the inlet, the ethyl chloride equivalent is the ethyl chloride concentration in ppmv. If another chlorine-containing promoter (specifically vinyl chloride, methyl chloride or ethylene dichloride) is used alone or in conjunction with ethyl chloride, the ethyl chloride equivalent is the concentration of ethyl chloride in ppmv plus the concentration of the other gaseous chloride-containing promoter (corrected for its effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed of 1 ppm ethylene dichloride and 1 ppm ethyl chloride, the ethyl chloride equivalent in the numerator of $Z^*$ would then be 3 ppmv.

The ethane equivalent is the concentration of ethane in mole percent plus the concentration of the other hydrocarbons effective in removing chloride from the catalysts, corrected for their effectiveness for dechlorination relative to ethane. The relative effectiveness of a non-ethane hydrocarbon can be measured experimentally by replacing ethane with the other hydrocarbon and determining the concentration needed to obtain the same level of catalyst performance provided by ethane when used as a dechlorinating agent. As a way of further illustration, if a concentration of ethylene at the reactor inlet of 10.0 mole percent is experimentally found to be equivalent in effectiveness in catalyst dechlorination to 0.1 mole percent ethane, then the ethane equivalent for 10.0 mole percent ethylene would be 0.1 mole percent. For a typical inlet reactor feed having 30.0 mole percent ethylene and 0.1 mole percent ethane, the ethane equivalent then will be 0.4 mole percent. If a hydrocarbon compound is found to have a very small dechloriding effect and is also present in low concentrations, then its contribution to the ethane equivalent concentration in the $Z^*$ calculation will be negligible.

It is important that the relative effectiveness of the gaseous chlorine-containing promoter and the hydrocarbon dechlorinating species also be measured under the reactor conditions which are being used in the process.

In the present invention, the useful range of concentration of the gaseous chlorine-containing promoter, expressed as $Z^*$, is from 5 to 40 ppmv.

Although the gaseous chlorine-containing promoter may be supplied as a single species, upon contact with the catalyst, other species may be formed leading to a mixture in the gas phase. Consequently, if the reaction gases are recycled, a mixture of species will be found in the inlet of the reactor. In particular, the recycled reaction gases at the inlet may contain ethyl chloride, vinyl chloride, ethylene dichloride and or methyl chloride, even though only ethyl chloride is supplied to the system. The concentrations of these chlorine-containing species must be considered in calculating $Z^*$. Reactions of the gaseous nitrogen-containing promoter on the catalyst surface will also occur, and species present in the recycle must be considered when calculating $N^*$.

While $Z^*$ is dependent on the concentration of particular hydrocarbons present in the feed gas, $N^*$ does not depend on the concentration of hydrocarbon species in the reactor within the ranges specified. While the present invention should be understood as being unconstrained by any particular theory, it is believed that the hydrocarbon species are less effective in removing the nitrogen-containing species present on the catalyst surface as compared to their effectiveness in removing the chlorine-containing species present on the catalyst surface.

When using the catalysts deployed in the process of this invention, it is necessary to optimize the inlet concentrations of both gaseous promoters, that is the nitrogen-containing promoter and the chlorine-containing promoter. The concentrations may be chosen to optimize one or more of the following catalyst performance measures: efficiency, activity (temperature), efficiency aging or activity (temperature) aging, thus several optima may exist depending on which aspects of catalyst performance have the greatest value to the user. The optimum performance of the catalyst has been found to depend on both gaseous promoter concentrations, that is some promoter combinations lead to much higher efficiency, activity, or slower aging than others. In particular, $N^*$ and $Z^*$ combinations where $N^*/Z^*$ is less than or equal to 1 have been found to provide better performance.

For each catalyst, the particular $N^*$ and $Z^*$ combination which gives the optimum performance will vary depending on the amount and type of solid promoter on the catalyst, the temperature of reaction, the concentration of carbon dioxide in the reactor, and the total amount of ethylene oxide produced since the first use of the catalyst, that is the catalyst age. $N^*$ will range from 1 to 20 ppmv, and $Z^*$ from 5 to 40 ppmv under the specified reaction conditions. Generally, for $N^*$, the values at the lower end of the range will be optimal at the beginning of catalyst operation when temperature, catalyst age and carbon dioxide levels are generally lower, and will shift to those at the higher end of the ranges after the catalyst has operated for a period of time, that is when the catalyst is older. Likewise, the optimum $Z^*$ value increases over time.

Higher temperature is thought to increase the optimum value of both $N^*$ and $Z^*$, while catalyst age increases the optimum $N^*$. The instantaneous ethylene oxide concentration is also thought to have a small effect on the optimum in that higher values of $N^*$ may be tolerated in catalysts making higher levels of ethylene oxide. While the present invention should be understood as being unconstrained by any particular theory, it is believed that higher $N^*$ and $Z^*$ are preferred at higher temperatures because the surface species produced by the nitrogen-containing promoter and the chlorine-containing promoter have lower residence time on the surface of the catalyst and/or the stability of particular species on the surface are dependent on the temperature. The temperature dependence is slightly greater for $Z^*$ than $N^*$, so $N^*/Z^*$ should be decreased slightly for an increase in reaction temperature given the same carbon dioxide level and catalyst age.

The optimum $N^*$ also depends on the concentration of carbon dioxide in the reactor, with higher $N^*$ generally being preferred at higher carbon dioxide concentrations. The average carbon dioxide concentration, that is average of the inlet and outlet carbon dioxide concentrations, affects the optimum $N^*$ in a tubular reactor, while the outlet carbon dioxide concentration has the most effect on the optimum $N^*$ in a continuously-stirred or back-mixed reactor.

Other conditions being similar, a solid catalyst which has produced larger cumulative quantities of EO will have a higher $N^*$ optimum than one which has made smaller cumulative amounts of EO.

Although ratios of $N^*/Z^*$ less than or equal to 1 are preferred for the process of the present invention, some ranges of the ratio are more preferred. For catalysts at the beginning of life with average carbon dioxide concentrations of less than or 1 percent, $N^*/Z^*$ ranging from 0.1 to 0.6 is preferred, particularly for high absolute efficiency and low efficiency aging of the catalyst. For older catalysts which have produced more than 1.1 kilo metric tons of ethylene oxide per m3 of catalyst (70,000 pounds of ethylene oxide per cubic foot of catalyst), a $N^*/Z^*$ ratio of 0.4 to 1.0 is preferred for high efficiency and lower efficiency aging. Activity may be increased by increasing the $N^*/Z^*$ ratio beyond the efficiency optimum.

When the concentration of carbon dioxide in the reactor inlet is greater than 2 mole percent, enhanced performance of a catalyst may still be realized with $N^*/Z^*$ ratios as high as 1.5.

When optimizing $N^*/Z^*$, it may be necessary to allow the catalyst to operate for at least 24 hours after making a change in operating conditions in order to determine the effect of the change on the steady state catalyst performance.

Although the present invention is described herein for use in the production of ethylene oxide, propylene oxide can be produced from propylene by a similar process to that for producing ethylene oxide using the present invention.

In commercially useful catalysts for the production of ethylene oxide, the carrier upon which the silver and promoters reside must have a physical form and strength to allow proper flow of gaseous reactants, products and ballast through the reactor while maintaining physical integrity over catalyst life. Significant catalyst breakage or abrasion is highly undesirable because of the pressure drop and safety problems such degradation can cause. The catalyst must also be able to withstand fairly large temperature fluctuations within the reactor. The pore structure and chemical inertness of the carrier are also important factors that must be considered for optimum catalyst performance. Refractory materials, particularly alpha-alumina, have been successfully used as the carrier for ethylene oxide catalysts. Other porous refractory carrier or materials may also be used as long as they are relatively inert in the presence of the reactant feeds introduced for epoxidation and the product epoxide, and are able to withstand preparation conditions when converted into catalyst. For example, carriers may be composed of alpha-alumina, silicon carbide, silicon dioxide, zirconia, magnesia, various clays and mixtures thereof. In the present invention, carrier comprised of alpha-alumina is preferred. Carriers containing modifiers which enhance the properties of the alpha-alumina as a catalyst carrier may also be used and may be preferred in some cases.

Suitable shapes for the carrier of this invention include any of the wide variety of shapes known for such catalyst supports, including pills, chunks, tablets, pieces, pellets, rings, spheres, wagon wheels, toroids having star shaped inner and/or outer surfaces, of a size suitable for employment in fixed bed reactors. Conventional commercial fixed bed ethylene epoxide reactors are typically in the form of a plurality of parallel elongated tubes (in a suitable shell) 1 to 3 inches O.D. and 15-45 feet long filled with catalyst. In such fixed bed reactors, it is desirable to employ carrier formed into a rounded shape, such as, for example, spheres, pellets, rings, and tablets, having diameters from 0.1 inch to 0.8 inch.

Well-known methods of preparing carriers may be employed to prepare the carrier suitable for use in ethylene oxide catalysts. For example, an alpha-alumina support of at least 95 percent purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) that may be used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives.

The alpha-alumina carrier prepared by this particular method preferably has a pore size distribution wherein:

less than 20 percent (more preferably, 0 to 5 percent) by volume of the pores have a diameter of less than 0.1 micron;

5 to 30 percent (more preferably, 5 to 20 percent) by volume of the pores have a diameter of 0.1 to 0.5 microns;

7 to 30 percent (more preferably, 10 to 25 percent) by volume of the pores have a diameter of 0.5 to 1.0 micron;

greater than 10 percent (more preferably, 10 to 40 percent) by volume of the pores have a diameter of 1.0 to 10 microns;

greater than 20 percent (more preferably, 30 to 55 percent) by volume of the pores have a diameter of 10 to 100 microns; and 4 to 20 percent (more preferably, 6 to 20 percent) by volume of the pores have a diameter of at least 100 microns.

Another method for preparing a carrier having particularly suitable properties for ethylene oxide catalyst usage comprises mixing boehmite alumina (AlOOH) and/or gamma-alumina, peptizing the aluminas in an acidic mixture containing halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of alpha-alumina carrier as further illustrated in the examples.

The alpha-alumina carrier prepared by the method described above preferably has a specific surface area of at least 0.5 $m^2/g$ (more preferably from 0.7 $m^2/g$ to 10 $m^2/g$), a pore volume of at least 0.5 cc/g (more preferably from 0.5 cc/g to 2.0 cc/g), purity (exclusive of any modifier component) of at least 99 weight percent alpha-alumina, and median pore diameter from 1 to 50 microns. In this case, the alpha-alumina carrier comprises particles each of which has at least one substantially flat major surface having a lamellate or platelet morphology which approximates the shape of a hexagonal plate (some particles having two or more flat surfaces), at least 50 percent of which (by number) have a major dimension of less than 50 microns.

Catalysts for the production of alkylene oxide, for example ethylene oxide or propylene oxide, may be prepared on the supports by impregnating the carrier with a solution of one or more silver compounds, as is well known in the art. One or more promoters may be impregnated simultaneously with the silver impregnation, before the silver impregnation and or after the silver impregnation. In making such a catalyst, the carrier is impregnated (one or more times) with one or more silver compound solutions sufficient to allow the silver to be supported on the carrier in an amount which ranges of from 1 percent to 70 percent, more preferably from 5 percent to 50 percent, most preferably from 10 percent to 40 percent of the weight of the catalyst.

The silver particle size is, though important, not narrowly critical. Suitable silver particle size can be in the range of from 100 to 10,000 angstroms.

There are a variety of known promoters, that is, materials which, when present in combination with particular catalytic materials, for example silver, benefit one or more aspect of catalyst performance or otherwise act to promote the catalyst's ability to make a desired product, for example ethylene oxide. Such promoters in themselves are generally not considered catalytic materials. The presence of such promoters in the catalyst has been shown to contribute to one or more beneficial effects on the catalyst performance, for example, enhancing the rate or amount of production of desired product, reducing the temperature required to achieve a suitable rate of reaction, reducing the rates or amounts of undesired reactions, etc. As described previously, promoters may be present in a solid form in the catalyst or added in a gaseous form to the reaction system. Gaseous promoters have been described as gas-phase modifiers, inhibitors and enhancers. In the catalysts and process of the present invention, an additional gas phase promoter comprising nitrogen moiety is also required for optimum performance of the catalyst. Competing reactions occur simultaneously in the reactor, and a critical factor in determining the effectiveness of the overall process is the measure of control one has over these competing reactions. A material which is termed a promoter of a desired reaction can be an inhibitor of another reaction, for example, a combustion reaction. What is significant is that the effect of the promoter on the overall reaction is favorable to the efficient production of the desired product, for example, ethylene oxide.

It is desirable that the silver and one or more solid promoters be relatively uniformly dispersed on the carrier. A preferred procedure for depositing silver catalytic material and one or more promoters comprises: (1) impregnating a porous carrier according to the present invention with a solution comprising a solvent or solubilizing agent, silver complex and one or more promoters upon the carrier, and (2) thereafter treating the impregnated carrier to convert the silver salt to silver metal and effect deposition of silver and the promoter(s) onto the exterior and interior pore surfaces of the carrier. Depositions of silver and solid promoters are generally accomplished by heating the carrier at elevated temperatures to evaporate the liquid within the carrier and effect deposition of the silver and promoters onto the interior and exterior carrier surfaces. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

The silver solution used to impregnate the carrier is preferably comprised of a silver compound in a solvent or complexing/solubilizing agent such as the silver solutions disclosed in the art. The particular silver compound employed may be chosen, for example, from among silver complexes, silver nitrate, silver oxide or silver carboxylates, such as silver acetate, oxalate, citrate, phthalate, lactate, propionate, butyrate and higher fatty acid salts. Silver oxide complexed with amines is a preferred form of silver for use in the present invention.

A wide variety of solvents or complexing/solubilizing agents may be employed to solubilize silver to the desired concentration in the impregnating medium. Among those disclosed as being suitable for this purpose are lactic acid; ammonia; alcohols, such as ethylene glycol; amines and aqueous mixtures of amines.

For example, $Ag_2O$ can be dissolved in a solution of oxalic acid and ethylenediamine to an extent of approximately 30 percent by weight. Vacuum impregnation of such a solution onto a carrier of approximately 0.7 cc/g porosity typically results in a catalyst containing approximately 25 percent by weight of silver based on the entire weight of the catalyst. Accordingly, if it is desired to obtain a catalyst having a silver loading of greater than 25 or 30 percent, and more, it would generally be necessary to subject the carrier to at least two or more sequential impregnations of silver, with or without promoters, until the desired amount of silver is deposited on the carrier. In some instances, the concentration of the silver salt is higher in the latter impregnation solutions than in the first. In other instances, approximately equal amounts of silver are deposited during each impregnation. Often, to effect equal deposition in each impregnation, the silver concentration in the subsequent impregnation solutions may need to be greater than that in the initial impregnation solutions. In further instances, a greater amount of silver is deposited on the carrier in the initial impregnation than that deposited in subsequent impregnations. Each of the impregnations may be followed by roasting or other procedures to render the silver insoluble.

The catalysts used in the process of this invention contain at least one or more promoters or modifiers added during the preparation of the catalyst to enhance the performance of the catalyst, for example to enhance efficiency or reduce the burning of ethylene oxide or affect activity. These promoters or modifiers are generally provided as chemical compounds.

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions.

The catalysts used in the process of this invention are of the type comprising at least one efficiency-enhancing salt of a member of a redox-half reaction pair and are utilized in the presence of a gaseous nitrogen-containing component capable of forming a gaseous efficiency-enhancing member of a redox-half reaction pair under reaction conditions. The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213-1218 (1961) or "CRC Handbook of Chemistry and Physics", 65th Edition, CRC Press, Inc., Boca Raton, Fla., pages D155-162 (1984). The term "redox-half reactions pair" refers to the pairs of atoms, molecules or ions or mixtures thereof which undergo oxidation or reduction in such half-reaction equations. Such terms as redox-half reaction pairs are used herein to include those members of the class of substance which provide the desired performance enhancement, rather than a mechanism of the chemistry occurring. Preferably, such compounds, when associated with the catalyst as salts of members of a half reaction pair, are salts in which the anions are oxyanions, preferably an oxyanion of a polyvalent atom; that is, the atom of the anion to which oxygen is bonded is capable of existing, when bonded to a dissimilar atom, in different valence states. Potassium is the preferred cation, although sodium, rubidium and cesium may also be operable, and the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred. As used herein, the term "salt" does not imply that the anion and cation components of the salt be associated or bonded in the solid catalyst, but only that both components be present in some form in the catalyst under reaction conditions.

The salt of a member of a redox-half reaction pair is added to the catalyst in an amount sufficient to enhance the efficiency of the epoxidation reaction. The precise amount will vary depending upon such variables as the gaseous efficiency-enhancing member of the redox-half reaction used and concentration thereof, the concentration of other components in the gas phase, the amount of silver contained in the finished catalyst as well at the time of promoter deposition, the surface area of the support, the process conditions, for example space velocity and temperature, and morphology of support. Alternatively, a suitable precursor compound may also be added such that the desired amount of the salt of a member of a redox-half reaction pair is formed in the catalyst under epoxidation conditions, especially through reaction with one or more of the gaseous components. Generally, however, a suitable range of concentration of the added efficiency-enhancing salt, or precursor thereof, calculated as cation, is 0.01 to 5 percent, preferably 0.02 to 3 percent, by weight, based on the total weight of the catalyst. Most preferably the salt is added in an amount of 0.03 to 2 weight percent.

The preferred gaseous efficiency-enhancing members of redox-half reaction pairs are compounds containing an element capable of existing in more than two valence states, preferably nitrogen and another element which is, preferably, oxygen. Examples of preferred gaseous efficiency-enhancing members of redox-half reaction pairs include at least one of NO, $NO_2$, $N_2O_4$, $N_2O_3$ or any gaseous substance capable of forming one of the aforementioned gases, particularly NO and $NO_2$, under epoxidation conditions. NO is most preferred as the gaseous-efficiency enhancing compound.

Although in some cases it is preferred to employ members of the same half-reaction pair in the reaction system, that is, both the efficiency-enhancing salt member associated with the catalyst and the gaseous member in the feedstream, as, for example, with a preferred combination of potassium nitrate and nitric oxide, this is not necessary in all cases to achieve satisfactory results. Other combinations, such as $KNO_2$/$N_2O_3$, $KNO_3$/$NO_2$, $KNO_3$/$N_2O_4$, $KNO_2$/NO, $KNO_2$/$NO_2$ may also be employed in the same system. In some instances, the salt and gaseous members may be found in different half-reactions which represent the first and last reactions in a series of half-reaction equations of an overall reaction.

In addition to the at least one salt of a redox half-reaction pair, the catalyst may additionally contain other solid promoters. For example, the additional promoters may comprise compounds containing the alkali metals, alkaline earth metals, halides, for example fluorides and chlorides, and the oxyanions of the elements other than oxygen having an atomic number of 5 to 83 of Groups 3b to 7b and 3a to 7a of the Periodic Table, or mixtures thereof. (References to the Periodic Table herein shall be to that as published by the Chemical Rubber Company, Cleveland, Ohio, in CRC Handbook of Chemistry and Physics, 46th Edition, inside back cover.) These compounds may be added in the form active in the catalyst or in another form which converts to the active species after preparation and use of the catalyst, and may exist in one or more forms in the catalyst.

Another class of promoters that may be added to the catalysts useful in the process of the present invention includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion. To stabilize the manganese component in the impregnating solution, it may be necessary to add a chelating compound such as ethylenediaminetetraaceticacid (EDTA) which serves to keep the manganese-containing ion in solution until it is impregnated and turned into solid form in the catalyst.

In any event, the promoters are provided in a promoting amount onto the solid catalyst. As used herein the term "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to maximize profits by taking into account feedstock costs, energy costs, and by-product removal costs.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other promoters, activators, stabilizers, enhancers or other catalyst improvers can also affect the promoting effects.

The process using silver catalysts of the present invention are particularly suitable for use in the production of ethylene oxide by vapor phase oxidation of ethylene with molecular oxygen in the oxygen-based process where high-purity (>95 mole percent) oxygen is employed as the source of the oxidizing agent, see Kirk-Othmer's *Encyclopedia of Chemical Technology*, $4^{th}$ Ed.(1994) Volume 9, p. 930-934.

Ethylene Epoxidation Conditions

A standard back-mixed autoclave with gas recycle is used for catalyst testing in the following examples. Well known, back-mixed, bottom-agitated "Magnedrive" autoclaves described in FIG. 2 of the paper by J. M. Berty entitled "Reactor for Vapor Phase-Catalytic Studies," in Chemical Engineering Progress, Vol. 70, No. 5, pages 78-84, 1974, are used as the reactors. Inlet conditions, including feeds, flows and temperatures are given in each of the examples.

The pressure is maintained at 1.79 kPa(kilopascals) (275 psig (pounds per square inch, gauge)) and the total inlet flow is maintained from 225 to 625 SCLH (standard cubic liter per hour) (8 to 22 SCFH (standard cubic feet per hour)). SCLH refers to cubic liter per hour at standard temperature and pressure, namely, 0° C. and one atmosphere. Temperature (° C.), percent outlet ethylene oxide, and catalyst efficiency are obtained as the responses describing the catalyst performance. Gas feeds contain ethylene, oxygen, carbon dioxide (optional), ethane (optional), ethyl chloride, nitric oxide and nitrogen as the ballast gas in all examples.

The catalyst test procedure used for autoclaves involves the following: 40 or 80 cc of catalyst is charged to the back-mixed autoclave and the weight of the catalyst is noted. The back-mixed autoclave is heated to reaction temperature in a nitrogen flow of 280 to 570 SCLH with the impeller operating at 1500 rpm. The nitrogen flow is then discontinued and the above-described feed stream is introduced into the reactor. The total gas inlet flow is then adjusted to the desired amount. Conditions are then adjusted to those desired for the test. The outlet epoxide concentration is monitored to make certain that the catalyst has reached its peak steady state performance. The efficiency of the catalyst to ethylene epoxide and the rate of deactivation (temperature rise and efficiency decline) may then be obtained. In determining activity and efficiency, the process and catalyst should be under steady state conditions.

The standard deviation of a single test result reporting catalyst efficiency in accordance with the procedure described above is 0.5 percent efficiency units. The typical standard deviation of a single test result reporting catalyst activity in accordance with the procedure described above is 2° C. The standard deviation, of course, will depend upon the quality of the equipment and precision of the techniques used in conducting the tests, and thus will vary. These standard deviations are believed to apply to the test results reported herein.

Catalyst Preparation

The carriers were vacuum impregnated with a first impregnation silver solution typically containing 30 weight percent silver oxide, 18 weight percent oxalic acid, 17 weight percent ethylenediamine, 6 weight percent monoethanolamine, and 27 weight percent distilled water. The first impregnation solution was typically prepared by (1) mixing 1.14 parts of ethylenediamine (high purity grade) with 1.75 parts of distilled water; (2) slowly adding 1.16 parts of oxalic acid dihydrate (reagent grade) to the aqueous ethylenediamine solution such that the temperature of the solution does not exceed 40° C., (3) slowly adding 1.98 parts of silver oxide, and (4) adding 0.40 parts of monoethanolamine (Fe and Cl free).

The carrier was impregnated in an appropriately sized glass or stainless steel cylindrical vessel which was equipped with suitable stopcocks for impregnating the carrier under vacuum. A suitable separatory funnel which was used for containing the impregnating solution was inserted through a rubber stopper into the top of the impregnating vessel. The impregnating vessel containing the carrier was evacuated to approximately 1-2" mercury absolute for 10 to 30 minutes, after which the impregnating solution was slowly added to the carrier by opening the stopcock between the separatory funnel and the impregnating vessel. After all the solution emptied into the impregnating vessel (~15 seconds), the vacuum was released and the pressure returned to atmospheric. Following addition of the solution, the carrier remained immersed in the impregnating solution at ambient conditions for 5 to 30 minutes, and was thereafter drained of excess solution for 10 to 30 minutes.

The silver-impregnated carrier was then roasted as follows to effect reduction of silver on the catalyst surface. The impregnated carrier was spread out in a single layer on stainless steel wire mesh trays then placed on a stainless steel belt (spiral weave) and transported through a 2"×2" square heating zone for 2.5 minutes, or equivalent conditions were used for a larger belt operation. The heating zone was maintained at 500° C. by passing hot air upward through the belt and the catalyst particles at the rate of 7533 standard cubic liter per hour (SCLH) (266 standard cubic feet per hour (SCFH)). After being roasted in the heating zone, the catalyst was cooled in the open air to room temperature and weighed.

Next, the silver-impregnated carrier was vacuum impregnated with a second silver impregnation solution containing both the silver oxalate amine solution and the catalyst promoters. The second impregnation solution was composed of all of the drained solution from the first impregnation plus a fresh aliquot of the first solution, or a new solution was used. The promoters, added with stirring in order to solubilize them, were added in sufficient amounts to reach the desired target levels on the finished catalysts. Promoters and stabilizers included neat potassium nitrate, manganese EDTA ($K_2$MnEDTA) solution and diammonium EDTA solution. One equivalent of diammonium EDTA was added with the manganese promoter in order to increase the stability of the manganese-containing ion in the impregnation solution.

The impregnation, draining and roasting steps for this second impregnation were carried out analogously to the first impregnation.

The twice-impregnated carrier, that is the finished catalyst, was again weighed, and based upon the weight gain of the carrier in the second impregnation, the weight percent of silver and the concentration of the promoters were calculated (results given in Table I). In some cases, the preparation of a catalyst was carried out on a larger scale than that described here using suitable scale-up of equipment and methods. The finished catalyst was then employed in an ethylene epoxidation reaction, the results of which are given in the Examples.

The properties of the starting carrier materials and catalysts are shown in Table I.

TABLE I

Carrier and Catalyst Properties

|  | Catalyst | |
|---|---|---|
|  | 1<br>A | 2<br>B |
| Carrier Properties | | |
| Surface Area (m2/g) | 1.1 | 1.1 |
| Pore volume (cc/g) | 0.75 | 0.75 |
| Catalyst Properties | | |
| Ag (wt. percent) | 33.85 | 34.22 |
| K (ppm) | 1421 | 1372 |
| Mn (ppm) | 174 | 175 |

EXAMPLE 1

Two 40 cc. samples of Catalyst 1, weighing 31.3 g each, were run in two different reactors. In both tests, the start-up inlet conditions were 8.0 mole percent $O_2$, 30.0 mole percent $C_2H_4$, 5.0 ppmv ethyl chloride, and 5 ppmv NO at a temperature of 220° C. and total reactor flow of 269 SCLS (9.5 SCFH). No carbon dioxide or ethane were fed to the reactor inlet. Temperature was then increased to 240° C., and on Day 5, $C_2H_6$ was increased to 0.27 mole percent. Further changes are shown in Tables II and III; ethylene oxide is abbreviated EO in all tables. In Test A, where a ratio of N*/Z* less than 1 is maintained, the efficiency is higher and more stable.

TABLE II

Test A of Catalyst 1

| Day | Inlet ECL (ppm) | Z* | Inlet NO (ppm) | N* | Outlet EO (mol percent) | Efficiency (percent) | Outlet CO2 (mol percent) | N*/Z* | Temp. (° C.) |
|---|---|---|---|---|---|---|---|---|---|
| 5 | 9.5 | 17 | 7 | 6.1 | 2.10 | 87.9 | 0.59 | 0.36 | 240 |
| 7 | 9.5 | 17 | 7 | 6.0 | 2.07 | 87.8 | 0.58 | 0.36 | 240 |
| 21 | 9.5 | 17 | 7 | 6.2 | 1.88 | 87.9 | 0.53 | 0.37 | 240 |
| 22 | 9.4 | 17 | 7 | 6.1 | 2.10 | 85.9 | 0.27 | 0.37 | 250 |

TABLE III

Test B of Catalyst 1

| Day | Inlet ECL (ppm) | Z* | Inlet NO (ppm) | N* | Outlet EO (mol percent) | Efficiency (percent) | Outlet CO2 (mol percent) | N*/Z* | Temp. (° C.) |
|---|---|---|---|---|---|---|---|---|---|
| 5 | 9.5 | 17 | 7 | 6.1 | 2.10 | 87.6 | 0.61 | 0.37 | 240 |
| 7 | 5.0 | 8.8 | 11 | 9.6 | 2.23 | 85.8 | 0.74 | 1.09 | 240 |
| 21 | 5.0 | 8.8 | 11 | 9.5 | 2.11 | 84.9 | 0.76 | 1.09 | 240 |
| 22 | 5.0 | 8.7 | 11 | 9.6 | 2.28 | 82.5 | 0.98 | 1.10 | 250 |

EXAMPLE 2

An 80 cc sample of Catalyst 1, weighing 62.6 g., was run in a reactor without $CO_2$ feed (Test C). A 40 cc. sample of Catalyst 1, weighing 31.3 g., was run in a smaller reactor at the same inlet conditions (Test A). Other inlet conditions are shown in Table IV; ethyl chloride is abbreviated as ECl. In both cases, changing the amount of ethane in the inlet had no effect on efficiency as long as the ethyl chloride was adjusted to keep $Z^*$ and hence $N^*/Z^*$ constant.

TABLE IV

Tests C and A of Catalyst 1

| Test | Day | Reactor Flow SCLH (SCFH) | Inlet $O_2$ (mol %) | Inlet $C_2H_4$ (mol %) | Inlet $C_2H_8$ (mol %) | Outlet $CO_2$ (mol %) | Inlet ECl (ppm) | $Z^*$ | Inlet NO (ppm) | $N^*$ | $N^*/Z^*$ | Outlet EO (mol %) | Temp. (° C.) | Eff. (%) |
|---|---|---|---|---|---|---|---|---|---|---|---|---|---|---|
| C | 7 | 476 (16.8) | 8.5 | 25.0 | 0.00 | 0.42 | 4.3 | 16.6 | 5.7 | 5.0 | 0.30 | 1.64 | 230 | 88.6 |
| C | 8 | 476 (16.8) | 8.5 | 25.0 | 0.20 | 0.42 | 7.6 | 16.8 | 6.0 | 5.2 | 0.31 | 1.63 | 230 | 88.6 |
| A | 4 | 269 (9.5) | 8.0 | 30.0 | 0.00 | 0.59 | 5.0 | 16.7 | 6.8 | 5.9 | 0.35 | 2.11 | 240 | 87.9 |
| A | 5 | 269 (9.5) | 8.0 | 30.0 | 0.27 | 0.59 | 9.5 | 16.7 | 7.0 | 6.1 | 0.36 | 2.10 | 240 | 87.9 |

EXAMPLE 3

A sample of 80 cc of Catalyst 1, weighing 62.6 g., was tested in a reactor under conditions given in Table V; ethyl chloride is abbreviated as ECl. Table V shows the optimization of $N^*/Z^*$ for efficiency by varying ECl. Days 8 to 12 show a traverse in $Z^*$ values. The catalyst exhibits long-term stability at the $Z^*$ and $N^*$ values finally chosen on day 12, as demonstrated by the efficiencies at days 17 and 23, which decline slightly due to catalyst aging, but remain relatively high.

TABLE V

Test D - Optimization of $N^*/Z^*$ Gaseous Promoter Ratio

| Day | Inlet $O_2$ (mol %) | Inlet $CO_2$ (mol %) | Inlet $C_2H_4$ (mol %) | Inlet $C_2H_6$ (mol %) | Outlet $CO_2$ (mol %) | Inlet ECl (ppm) | $Z^*$ | Inlet NO (ppm) | $N^*$ | $N^*/Z^*$ | Outlet EO (mol %) | Eff. (%) | Temp. (° C.) | Reactor Flow |
|---|---|---|---|---|---|---|---|---|---|---|---|---|---|---|
| 8 | 8.2 | 0.3 | 24.6 | 0.2 | 0.72 | 6.5 | 14.5 | 6.0 | 5.2 | 0.36 | 1.48 | 88.9 | 230 | 481 (17.0) |
| 9 | 8.2 | 0.3 | 24.6 | 0.2 | 0.75 | 4.5 | 10.0 | 6.0 | 5.2 | 0.52 | 1.49 | 88.2 | 230 | 481 (17.0) |
| 10 | 8.2 | 0.3 | 24.6 | 0.2 | 0.71 | 7.4 | 16.6 | 6.1 | 5.3 | 0.32 | 1.44 | 88.7 | 230 | 481 (17.0) |
| 11 | 8.2 | 0.3 | 24.6 | 0.2 | 0.72 | 6.0 | 13.4 | 6.1 | 5.3 | 0.40 | 1.46 | 88.8 | 230 | 481 (17.0) |
| 12 | 8.2 | 0.3 | 24.6 | 0.2 | 0.72 | 6.5 | 14.5 | 6.2 | 5.3 | 0.37 | 1.45 | 88.9 | 230 | 481 (17.0) |
| 17 | 8.2 | 0.3 | 24.6 | 0.2 | 0.71 | 6.5 | 14.5 | 6.1 | 5.3 | 0.37 | 1.41 | 88.8 | 230 | 481 (17.0) |
| 23 | 8.2 | 0.3 | 24.6 | 0.2 | 0.70 | 6.5 | 14.5 | 6.1 | 5.3 | 0.37 | 1.38 | 88.7 | 230 | 481 (17.0) |

EXAMPLE 4

Two 40 cc. samples of Catalyst 2 with a weight of 31.3 g. each were run at the same time in different reactors. In both tests, the start-up inlet conditions were 8.0 mole percent $O_2$, 30.0 mole percent $C_2H_4$, 5.0 ppmv ethyl chloride and 5 ppmv NO at a temperature of 220° C. and total reactor flow of 269 SCLH (9.5 SCFH). No carbon dioxide or ethane were fed to the reactor inlet initially. Temperature was increased to 245° over the first three days. Further changes are shown in Tables VI and VII. Clearly, the selectivity and activity of Catalyst 2 is higher in Test A where the N*/Z* ratio is below 1, than in Test B where the ratio is greater than 1.

TABLE VI

Test A of Catalyst 2

| Day | Inlet ECL (ppm) | Inlet $C_2H_6$ (%) | Inlet $CO_2$ (%) | Z* | Inlet NO (ppm) | N* | Outlet EO (mol percent) | Efficiency (percent) | Outlet $CO_2$ (mol percent) | N*/Z* | Temp. (° C.) |
|---|---|---|---|---|---|---|---|---|---|---|---|
| 1 | 5.0 | 0.0 | 0.0 | 17 | 5 | 4.4 | 1.19 | 89.5 | 0.28 | 0.26 | 220 |
| 4 | 5.0 | 0.0 | 0.0 | 17 | 8 | 6.9 | 2.26 | 86.8 | 0.69 | 0.42 | 245 |
| 5 | 5.0 | 0.0 | 1.0 | 17 | 10 | 8.7 | 1.60 | 85.4 | 1.56 | 0.52 | 245 |
| 8 | 5.0 | 0.0 | 1.0 | 17 | 10 | 8.7 | 1.50 | 84.9 | 1.55 | 0.52 | 245 |

TABLE VII

Test B of Catalyst 2

| Day | Inlet ECL (ppm) | Inlet $C_2H_6$ (%) | Inlet $CO_2$ (%) | Z* | Inlet NO (ppm) | N* | Outlet EO (mol percent) | Efficiency (percent) | Outlet $CO_2$ (mol percent) | N*/Z* | Temp. (° C.) |
|---|---|---|---|---|---|---|---|---|---|---|---|
| 1 | 5.0 | 0.0 | 0.0 | 17 | 5.0 | 4.4 | 1.19 | 89.1 | 0.30 | 0.26 | 220 |
| 4 | 5.0 | 0.0 | 0.0 | 17 | 7.9 | 6.9 | 2.22 | 86.4 | 0.70 | 0.41 | 245 |
| 5 | 5.0 | 0.27 | 1.0 | 8.8 | 12.9 | 11.2 | 1.72 | 83.4 | 1.69 | 1.28 | 245 |
| 8 | 5.0 | 0.27 | 1.0 | 8.8 | 13.0 | 11.3 | 1.68 | 83.0 | 1.70 | 1.29 | 245 |

The invention claimed is:

1. A process for the manufacture of ethylene oxide through the epoxidation of ethylene in a reactor having at least one inlet for the introduction of raw materials and additives and at least one outlet for the discharge of ethylene oxide, which process comprises:

A) reacting a feed comprising ethylene, oxygen, and optionally ethane in the presence of a catalyst, said catalyst comprising a catalytically-effective amount of silver on an inert, refractory solid support and at least one efficiency-enhancing salt of a member of a redox-half reaction pair;

B) adding to said feed a two-component gas-phase promoter comprising at least one chlorine-containing component selected from a group consisting of ethyl chloride, methyl chloride, vinyl chloride and ethylene dichloride; and at least one nitrogen-containing component selected from a group consisting of nitric oxide and other compounds capable of forming under reaction conditions at least one gaseous efficiency-enhancing member of a redox-half reaction pair comprising NO, NO2, N2O3 or N2O4;

(C) after producing with such catalyst more than about 1.1 kilo metric tons of ethylene oxide per cubic meter of catalyst, adjusting the amount of each component of said gas-phase promoter to maintain the ratio of N* to Z* in the range of from 0.4 to 1.0, wherein, N* is defined as the nitric oxide equivalent, in units of ppmv, having an numerical value from 1 to 20 ppmv; wherein if nitric oxide is the only gaseous nitrogen-containing component present in the inlet, N* is the inlet nitric oxide concentration in ppmv multiplied by the inlet pressure in kilopascals, absolute, divided by 2300 kPa, and if one or more other gaseous nitrogen-containing components are used alone or in connection with nitric oxide, the nitric oxide equivalent is the concentration of nitric oxide in ppmv plus the concentration of each of the other gaseous nitrogen-containing components (each corrected for its effectiveness as a promoter as compared to nitric oxide) times the inlet pressure in kilopascals, absolute, divided by 2300 kPa; and Z*=ethyl chloride equivalent (ppmv) ×100 percent/ethane equivalent (mol percent)×100 having an numerical value of 5 to 40 ppmv, wherein if ethyl chloride is the only gaseous chloride-containing component present in the inlet, the ethyl chloride equivalent is the ethyl chloride concentration in ppmv, and if one or more other chloride-containing components are used alone or in combination with ethyl chloride, the ethyl chloride equivalent is the concentration of ethyl chloride in ppmv plus the concentration of each of the other gaseous chloride-containing components (each corrected for its effectiveness as a promoter as compared to ethyl chloride); and wherein the ethane equivalent is the concentration of ethane in mol percent plus the concentration of each other hydrocarbon effective in removing chloride from the catalyst (each corrected for its effectiveness in removing chloride from the catalyst as compared to ethane); and E) controlling the temperature of said reactor from 200° C. to 300° C., and the pressure at the inlet of said reactor from 1000 to 2500 kPa (absolute), and the concentration of carbon dioxide at said inlet from 0 to 2 mole percent.

2. The process of claim 1 wherein said efficiency-enhancing salt is potassium nitrate or rubidium nitrate.

3. The process of claim 1 wherein said silver is present from 5 to 50 percent by weight of the catalyst.

4. The process of claim 1 wherein said refractory solid support comprises alpha-alumina.

5. The process of claim 4 wherein said alpha-alumina support has a morphology comprising interlocking platelets.

6. The process of claim 1 wherein the temperature of said reactor is controlled from 210° C. to 280° C.

7. The process of claim 1 wherein the pressure at the inlet of said reactor is controlled from 1800 to 2500 kPa (absolute).

* * * * *

UNITED STATES PATENT AND TRADEMARK OFFICE
CERTIFICATE OF CORRECTION

PATENT NO. : 7,615,655 B2
APPLICATION NO. : 10/571508
DATED : November 10, 2009
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 823 days.

Signed and Sealed this

Nineteenth Day of October, 2010

David J. Kappos
*Director of the United States Patent and Trademark Office*